United States Patent [19]

Gray et al.

[11] Patent Number: 4,579,586

[45] Date of Patent: Apr. 1, 1986

[54] MERCAPTOHYDROXY ALKANES

[75] Inventors: Roy A. Gray; Gary D. Macdonell, both of Bartlesville, Okla.

[73] Assignee: Phillips Petroleum Company, Bartlesville, Okla.

[21] Appl. No.: 620,227

[22] Filed: Jun. 13, 1984

Related U.S. Application Data

[62] Division of Ser. No. 503,432, Jun. 13, 1983, Pat. No. 4,472,569.

[51] Int. Cl.$^4$ ............................................... B03D 1/02
[52] U.S. Cl. .......................................... 75/2; 209/162; 209/164; 209/5; 252/61; 423/26; 528/109
[58] Field of Search ............................ 209/162, 164, 5; 210/703; 252/61; 423/26; 75/2; 528/109

[56] References Cited

U.S. PATENT DOCUMENTS

| | | | |
|---|---|---|---|
| 2,633,458 | 3/1953 | Shokal | 260/45.2 |
| 3,086,997 | 4/1963 | Warner et al. | 260/609 |
| 3,355,512 | 11/1967 | De Acetis et al. | 260/830 |
| 3,394,192 | 7/1968 | Jones et al. | 260/609 |
| 3,662,004 | 5/1972 | Umbach et al. | 260/609 R |
| 3,755,463 | 8/1973 | Umbach et al. | 260/609 R |
| 3,803,089 | 4/1974 | Jones et al. | 260/47 EC |
| 4,472,569 | 9/1984 | Gray et al. | 528/109 |

OTHER PUBLICATIONS

Phillips Chemical Company Advertisement, 5/24/82, #25980-E.
Chemical Abstract, vol. 73, 346846.
Chemical Abstract, vol. 73, 16635d.
Chemical Abstract, vol. 73, 124807r.
Chemical Abstract, vol. 74, 87365.

*Primary Examiner*—John Doll
*Assistant Examiner*—Robert L. Stoll
*Attorney, Agent, or Firm*—L. M. Lavin

[57] ABSTRACT

Dimercaptodihydroxy alkanes are used as a curing agent for epoxide resins and as ore flotation agents.

4 Claims, No Drawings

MERCAPTOHYDROXY ALKANES

This application is a divisional application of my co-pending application Ser. No. 503,432 filed June 13, 1983, now U.S. Pat. No. 4,472,569.

This invention relates to mercaptohydroxy alkanes. It specifically relates to dimercaptodihydroxy alkanes. It also relates to the use of dimercaptodihydroxy alkanes as curing and flotation agents. In one aspect this invention relates to the use of dimercaptodihydroxy alkanes as curing agents for epoxy resins. In another aspect it relates to the use of dimercaptodihydroxy alkanes as ore flotation agents.

The methods of preparing mercaptohydroxy alkanes are known in the art. Mercaptohydroxy alkanes are produced by reacting compounds selected from mono- and poly-epoxides with about a stoichiometric amount of hydrogen sulfide at temperatures of from 20° C. to 200° C. at normal to elevated pressures in the presence of from 0.01 percent to 10 percent by weight, based on the weight of said epoxide of a strongly basic catalyst and recovering said mercaptohydroxy alkane.

Mercaptohydroxy alkanes have been shown to be useful as insecticides and fungicides. They have also been used as emulsifiers and antioxidants. The instant invention is a novel use for dimercaptodihydroxy alkanes. Dimercaptodihydroxy alkanes have been found to be a useful curing agent for epoxy resins and as ore flotation agents. In particular, 1,10-dimercapto-2,9-dihydroxydecane has been found to be a curing agent for epoxy resins and an ore flotation agent.

Epoxy resins are organic compounds containing at least one chemically reactive linkage known as an epoxy group. This group is formed by the the union of an oxygen atom with two vicinal covalently bonded carbon atoms. When curing agents are used with epoxy resins, the resins can be formulated, through well known means in the art, into coatings, adhesives and various plastics. Most cured epoxy resins are tough, hard products, generally adhering tenaciously to whatever substrate it is applied. The time required for a satisfactory cure is generally 1 to 24 hours depending on the activity of both the epoxy resin and the curing agent. Curing agents, such as pentaerythritol tetra(3-mercaptopropionate) have been used with epoxy resins and are well known in the art. One aspect of the present invention is to provide a novel epoxy resin curing agent.

Another aspect is to provide a compound useful as ore flotation agents. Froth flotation is a process for concentrating minerals from ores. In a froth flotation process the ore is crushed and wet ground to obtain a pulp. Additives such as collecting agents and frothing agents are added to the pulp to assist in subsequent flotation steps and the valuable minerals are separated from the undesired gangue portions of the ore. After flotation agents are added the pulp is aerated to produce a froth. The minerals which adhere to the bubbles or froth are skimmed or otherwise removed from the surface of the flotation liquid and the mineral adhering froth is collected and further processed to obtain the desired minerals. Some minerals such as chrysocolla, a metal silicate, $CuSiO_3$, generally are not separated from ores by flotation but rather by acid leaching because of the difficulty is satisfactorily floating the material. One aspect of the present invention is to provide a flotation agent for these minerals.

Therefore, an object of this invention is to provide a dimercaptodihydroxy alkane. Another object of this invention is to provide a curing agent for epoxy resins. Another object is to provide an ore flotation agent. Another object of this invention is to provide a novel compound. These and other objects will become apparent as the description thereof proceeds.

STATEMENT OF THE INVENTION

The instant invention provides a dimercaptodihydroxy alkane. In particular it provides a novel compound 1,10-dimercapto-2,9-dihydroxydecane. In accordance with one embodiment of the invention, it has been found that dimercaptodihydroxy alkanes are useful as curing agents for epoxy resins. In accordance with another embodiment of the invention it has been found that dimercaptodihydroxy alkanes are useful in ore flotation. In another embodiment of the invention it relates to a process of curing epoxy resins using dimercaptodihydroxy alkanes. In still another embodiment of the invention it relates to a process of separating metal silicate from ores using dimercaptodihydroxy alkanes.

The dimercaptodihydroxy alkanes suitable in this invention are of the following formula:

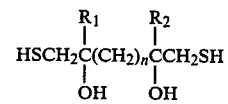

where n ranges from 0 to about 16, $R_1$ and $R_2$ can be any alkyl radical having from 1 to 16 carbon atoms or hydrogen. The total number of carbon atoms can be from 4 to about 20. Specific examples of dimercaptodihydroxy alkanes that can be used include 1,10-dimercapto-2,9-dihydroxydecane, 1,4-dimercapto-2,3-dihydroxybutane and 1,20-dimercapto-2,19-dihydroxyeicosane.

The instant invention is made by epoxidizing alpha, omega diolefins in any conventional manner to obtain a diepoxy alkane of the formula

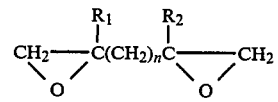

where n is from 0 to about 16. $R_1$ and $R_2$ can be any alkyl radical having from 1 to 16 carbon atoms or hydrogen. Examples of typical diolefins within the scope of this invention include 1,3-butadiene, 2-methyl-1,3-butadiene (isoprene), 1,4-pentadiene, 1,5-hexadiene, 1,6-heptadiene, 2,4-dimethyl-1,4-pentadiene, 1,7-octadiene, 1,8-nonadiene, 1,9-decadiene, 1,11-dodecadiene and 1,19-eicosadiene.

The diepoxy compound thus formed is reacted with about a stoichiometric amount of hydrogen sulfide at a suitable temperature and pressure. In general, the temperature can range from about 25° C. to 125° C. and the pressure from about 0 to 20 atmospheres. The reaction takes place in the presence of a suitable amount of a strongly basic catalyst. In general, the catalyst will be present in from about 0.01 percent to about 10 percent by weight, based on the weight of the diepoxy alkane. The strongly basic catalyst can be any suitable catalyst. In general, the catalyst will be selected from sodium hydroxide, potassium hydroxide and ammonium hydroxide. The dimercaptodihydroxy alkanes are then separated from the mixture in any conventional method.

The separated dimercaptodihydroxy alkane is then intimately mixed with an epoxy resin. This mixing may be done in any conventional manner. The mixing should continue until a homogenous mixture is achieved.

The dimercaptodihydroxy alkanes can be used in curing any epoxy, diepoxy or polyepoxy resins. In the preferred invention, the epoxy resin can be the diglycidyl ether of bisphenol A, known commercially as EPON 828.

The dimercaptodihydroxy alkane and the epoxy resin can be combined in any ratio sufficient to effect a cure of the epoxy resin. In general they will be combined in a ratio from about 0.75 equivalents mercaptan per equivalent of epoxy to about 1.3 equivalents mercaptan per equivalent of epoxy resin. In the preferred embodiment of the invention the ratio is about 1:1 equivalents of mercaptan to an equivalent of epoxy.

The dimercaptodihydroxy alkanes can also be used with any suitable catalyst for curing epoxide resins. The purpose of the catalyst is to initiate the reaction between the mercaptan groups of the dimercaptodihydroxy alkane and the epoxy groups of the epoxy resin. In the preferred embodiment, dimercaptodihydroxy alkanes can be used with catalyst selected from tertiary amines such as tris(dimethylaminomethyl)phenol(DMP-30), triethylamine and $N,N,N',N'$-tetramethylethylenediamine.

These dimercaptodihydroxy alkanes can also be used in combination with accelerators, solvents, pigments, thickeners, fillers or any other additives used with epoxy resins. The dimercaptodihydroxy alkanes can be used in any epoxide application. The application areas could be, for example, coatings, adhesives, sealants, and the like.

Dimercaptodihydroxy alkanes can also be used as ore flotation agents. In this embodiment of the invention the flotation agent is added to the crushed and wet ground ore, known as the pulp.

The amount of flotation agent employed can vary considerably depending upon the mineral concentration, the pH of the pulp, and the mineral being floated. Generally the dimercaptodihydroxy alkane flotation agent will be used in a range from about 0.005 pounds per ton of ore or solid to about 20 pounds per ton of ore or solid.

It is generally believed that the dimercaptodihydroxy alkanes disclosed herein are useful for separating any valuable metal from its corresponding gangue material. It is also understood that the dimercaptodihydroxy alkanes may separate a mixture of metals that are contained in a particular mining deposit or ore, said mixture being further separated by subsequent froth flotations or any other conventional separating methods. The dimercaptodihydroxy alkanes herein disclosed are particularly useful for separating silicate containing minerals from the total ore, such as chyrsocolla.

Other metal bearing ores within the scope of this invention are, for example, but not limited to, such materials as:

| Molybdenum-Bearing Ores | |
|---|---|
| Molybdenite | $MoS_2$ |
| Wulfenite | $PbMoO_4$ |
| Powellite | $Ca(MoW)O_4$ |
| Ferrimolybdite | $Fe_2Mo_3O_{12}.H_2O$ |

| -continued | |
|---|---|
| Copper-Bearing Ores | |
| Covallite | $CuS$ |
| Chalcocite | $Cu_2S$ |
| Chalcopyrite | $CuFeS_2$ |
| Bornite | $Cu_5FeS_4$ |
| Cubanite | $Cu_2SFe_4S_5$ |
| Valerite | $Cu_2Fe_4S_7$ or $Cu_3Fe_4S_7$ |
| Enargite | $Cu_3(As,Sb)S_4$ |
| Tetrahedrite | $Cu_3SbS_2$ |
| Tennanite | $Cu_{12}As_4S_{13}$ |
| Cuprite | $Cu_2O$ |
| Tenorite | $CuO$ |
| Malachite | $Cu_2(OH)_2CO_3$ |
| Azurite | $Cu_3(OH)_2CO_3$ |
| Antlerite | $Cu_3SO_4(OH)_4$ |
| Brochantite | $Cu_4(OH)_6SO_4$ |
| Atacamite | $Cu_2Cl(OH)_3$ |
| Chrysocolla | $CuSiO_3$ |
| Famatinite | $Cu_3(Sb,As)S_4$ |
| Bournonite | $PbCuSbS_3$ |
| Stannite | $Cu_3FeSnS_4$ |
| Lead-Bearing Ore | |
| Galena | $PbS$ |
| Antimony-Bearing Ore | |
| Stibnite | $Sb_2S_3$ |
| Zinc-Bearing Ore | |
| Sphalerite | $ZnS$ |
| Zincite | $ZnO$ |
| Smithsonite | $ZnCO_3$ |
| Silver-Bearing Ore | |
| Argentite | $Ag_2S$ |
| Stephanite | $Ag_5SbS_4$ |
| Hessite | $AgTe_2$ |
| Chromium-Bearing Ore | |
| Daubreelite | $FeSCrS_3$ |
| Chromite | $FeO.Cr_2O_3$ |
| Gold-Bearing Ore | |
| Sylvanite | $AuAgTe_2$ |
| Calaverite | $AuTe$ |
| Platinum-Bearing Ore | |
| Cooperite | $Pt(AsS)_2$ |
| Sperrylite | $PtAs_2$ |
| Uranium-Bearing Ore | |
| Pitchblende | $U_2O_5(U_3O_8)$ |
| Gummite | $UO_3.nH_2O$ |

These minerals are often associated with other valuable ores which can be separated together from gangue or waste material during an initial flotation process or which can be separated in the initial flotation process by using depressants. Dimercaptodihydroxy alkanes of the present invention can be used with any suitable flotation depressants for separation of valuable ores.

Any froth flotation apparatus can be used with this invention. Most commonly used commercial flotation machines are the Agitair (Gallagher Co.), Denver (Denver Equipment Company), and the Fagergren (Western Machinery Company). Smaller, laboratory scale apparatus, such as a Hallimond cell, can also be used.

The instant invention was demonstrated in tests conducted at ambient room temperature and at atmospheric pressure. However, any temperature or pressure generally employed by those skilled in the art are within the scope of this invention.

The advantages of this invention are further illustrated by the following examples.

EXAMPLE I

This example describes the preparation of the inventive compound 1,10-dimercapto-2,9-dihydroxydecane from 1,9-decadiene. A solution of 17.3 grams (0.13 mole) of freshly distilled 1,9-decadiene and 200 milliliters of methylene chloride was placed in a 1-liter round-bottom flash equipped with thermometer, stirrer and dropping funnel. Fifty-four and one-half grams (0.27 mole) Aldrich 85 percent m-chloroperbenzoic acid in 600 milliliters methylene chloride was added dropwise to the stirred solution over about two hours keeping the temperature at 25°-30° C. with the aid of a water/ice bath. After addition of the m-chloroperbenzoic acid the stirring was continued for four hours. The solid was filtered and washed twice with 200 milliliters of methylene chloride. The organic phases were combined, washed with 5 percent sodium sulfite to destroy any unreacted peracid, then with 5 percent sodium bicarbonate to remove the acid and dried over Drierite. The methylene chloride was stripped off on a rotary evaporator at room temperature with the aid of a vacuum pump. The product was fractionated to recover 1,9-decadiene, b.p. 48° C. at 15 mmKg., 1,2-epoxy-9-decene, b.p. 84° C. at 10 mmKg., and 1,2,9,10-diepoxydecane, b.p. 88° C. at 0.5 mmKg.

Five grams of sodium hydroxide dissolved in 300 milliliters methyl alcohol and 104 grams hydrogen sulfide was charged to a 1-liter stainless steel reactor. The reaction mixture was heated to 65° C. and 136 grams (0.80 moles) of 1,2,9,10-diepoxydecane was pumped in over a 35 minute period. After the addition was complete the reaction mixture was maintained at 65° C. for 1½ hours and at 93° C. for 1 hour. The reaction mixture was cooled, excess hydrogen sulfide vented and drained. The crude reaction mixture was purged with nitrogen for 15 minutes followed by acidification with concentrated hydrochloric acid. Solvent was stripped on rotary evaporator using steam heat and a water aspirator. The product was suction filtered hot and it solidified on standing to give 162 grams of a white solid, 1,10-dimercapto-2,9-dihydroxydecane.

EXAMPLE II

This example describes the evaluation of 1,10-dimercapto-2,9-dihydroxydecane as a curing agent for epoxy resins. To a beaker was added 5 grams (0.0263 equivalents) of an epoxy resin Epon 828 (diglycidyl ether of bisphenol A), 3.2 grams (0.0268 equivalents) of the dimercapto dihydroxy decane prepared in Example I, 3 grams of methyl ethyl ketone (2-butanone) solvent and 0.25 grams of DMP-30 catalyst, tris(2,4,6-dimethylaminomethyl)phenol. The mixture was stirred rapidly and a thermometer immersed in the mixture to measure temperature rise. After about 15 minutes the mixture became visibly too thick to pour, referred herein as open time. After about 30 minutes the mixture became solid and was accompanied by an exotherm, the maximum temperature reached was 90° C. (194° F.). This is the inventive run 5 listed in Table I. The experiment was repeated except the dimercaptodihydroxy decane was replaced with 1,10-dimercaptodecane. This run, No. 4, indicated a much slower cure rate compared to the inventive run 5. Open time was over 2 hours. It did not become solid within 24 hours nor was there any significant exotherm although it did cure but required a much longer time. Thus, it appears the presence of hydroxy groups is beneficial in increasing the reactivity of the mercaptan group of the inventive compound.

Other control runs were made, Nos. 1, 2, 3, to determine curing rate of the epoxy resin with other curing systems. The most closely related run was No. 2 in which another mercaptan curing agent was used, namely, pentaerythritol tetra(3-mercaptopropionate). This tetramercaptan curing agent performed comparably to the inventive dimercaptodihydroxy decane.

TABLE I

| | Effect of Epoxy Resin Curing Agents | | | | |
|---|---|---|---|---|---|
| Run | | Control | | | Invention |
| No.: | 1 | 2 | 3 | 4 | 5 |
| A. Composition, grams | | | | | |
| 1 Epon 828 | 5 | 5 | 5 | 5 | 5 |
| 2 DMP-30 (catalyst) | .25 | .25 | .25 | .25 | .25 |
| 3 Q-43[a] | — | 3.2 | — | — | — |
| 4 1,10-Dimercaptodecane | — | — | 3.2 | 3.2 | — |
| 5 1,10-Dimercapto-2,9-dihydroxydecane | — | — | — | — | — |
| 6 MEK solvent | — | — | — | 3 | 3 |
| B. Mixing | | | | | |
| 1 Maximum Exotherm, °C. | 37 | 110 | 30 | 31 | 90 |
| Maximum Exotherm, °F. | 98 | 230 | 85 | 87 | 194 |
| 2 Mins. to Solid | 37 | 27 | >24 hrs. | >24 hrs. | 30 |
| 3 Open Time, mins. | 17 | 23 | — | 140 | 15 |

[a]Pentaerythritol tetra(3-mercaptopropionate) from Evans Chemetics.

EXAMPLE III

This example illustrates the use of the inventive compound 1,10-dimercapto-2,9-dihydroxydecane as an ore flotation reagent using the Hallimond cell. Reasonably pure mineral, chrysocolla, was employed to more accurately measure efficiency of the collector without interference from other materials such as gangue or sulfide ores. Other similar compounds were also tested as controls. The following is a typical procedure. To a 170 milliliter capacity Hallimond cell was charged two grams of granulated chrysocolla, $CuSiO_3$, and about 69 milliliters of demineralized water (pH=6.5, resistivity >1 million $\Omega$) and the pH measured. Generally, the pH was above 7 and had to be lowered below 7 by the addition of dilute (10-20 percent) sulfuric acid. Additional water was added, 100 milliliters, and the mineral conditioned in the cup (70 milliliter capacity) for about 1 minute while magnetic agitation was applied and maintained constant by a magnetic field, revolving at about 800 rpm. A flow of nitrogen, measured by a calibrated capillary (F and P Co., Precision Bore Flowrator Tube No. 08F-1/16-08-5136), was also maintained constant at 4 cfs. Flotation was then carried out for 2 minutes. The floated fractions (concentrate) were then filtered, oven dried at 82° C. (180° F.) for 24 hours and weighed. From this weight the percent recovery of the mineral was estimated. This evaluation is listed in Table II where it can be seen that the inventive compound (Run 5) floats chrysocolla, a heretofore difficult mineral to float. The data also show, the effectiveness of the inventive compound to act as a collector is comparable to other dimercaptans but which do not contain the hydroxy functionality.

TABLE II

| Effect of Dithiols as Mineral Collectors in Ore Flotation (2 grams Chrysocolla-Hallimond Cell) | | | |
|---|---|---|---|
| Run No. | Collector | lbs/Ton | Wt. % Recovery |
| 1 | 1,3-propanedithiol | 10 | 0 |
| 2 | 1,2-propanedithiol | 10 | 16 |
| 3 | 1,6-hexanedithiol | 15 | 22 |
| 4 | 1,10-decanedithiol | 10.3 | 20 |
| Invention: | | | |

TABLE II-continued

Effect of Dithiols as
Mineral Collectors in Ore Flotation
(2 grams Chrysocolla-Hallimond Cell)

| Run No. | Collector | lbs/Ton | Wt. % Recovery |
|---|---|---|---|
| 5 | 1,10-dimercapto-2,9-dihydroxydecane | 10.3 | 20 |

We claim:

1. A process for recovering minerals from an ore containing minerals, said process comprising in a froth flotation process admixing said ore with a dimercaptodihydroxy alkane of the formula

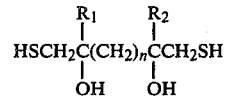

where n ranges from 0 to about 16 carbon atoms; $R_1$ is any alkyl radical having from 1 to about 16 carbon atoms or hydrogen; $R_2$ is any alkyl radical having from 1 to 16 carbon atoms or hydrogen; and the total number of carbon atoms can be from 4 to about 20, in an amount sufficient to aid in the flotation of said minerals and recovering the floated minerals.

2. A process as in claim 1 where said dimercaptodihydroxy alkane is 1,10-dimercapto-2,9-dihydroxydecane.

3. A process as in claim 1 where said dimercaptodihydroxy alkane is present in an amount ranging from about 0.005 pounds/ton to about 20 pounds/ton.

4. A process as in claim 1 wherein said mineral containing ore is chrysocolla ($CuSiO_3$).

* * * * *